(12) United States Patent
Hanabusa et al.

(10) Patent No.: US 9,750,676 B2
(45) Date of Patent: Sep. 5, 2017

(54) BASIC AMINO ACID DERIVATIVE THAT DEMONSTRATES A GELLING ABILITY IN A WATER SYSTEM

(71) Applicant: AJINOMOTO CO., INC., Tokyo (JP)

(72) Inventors: Kenji Hanabusa, Ueda (JP); Masahiro Suzuki, Ueda (JP); Takanori Sugimoto, Kawasaki (JP)

(73) Assignee: AJINOMOTO CO., INC., Tokyo (JP)

(*) Notice: Subject to any disclaimer, the term of this patent is extended or adjusted under 35 U.S.C. 154(b) by 158 days.

(21) Appl. No.: 14/453,036

(22) Filed: Aug. 6, 2014

(65) Prior Publication Data

US 2014/0348767 A1 Nov. 27, 2014

Related U.S. Application Data

(63) Continuation of application No. PCT/JP2013/053147, filed on Feb. 8, 2013.

(30) Foreign Application Priority Data

Feb. 9, 2012 (JP) ................................ 2012-025683
Jun. 29, 2012 (JP) ................................ 2012-146669

(51) Int. Cl.
| | | |
|---|---|---|
| *A61K 8/44* | (2006.01) | |
| *A61K 8/04* | (2006.01) | |
| *A61Q 19/10* | (2006.01) | |
| *A61Q 19/00* | (2006.01) | |
| *A61Q 5/00* | (2006.01) | |
| *A61Q 17/04* | (2006.01) | |
| *C07C 237/12* | (2006.01) | |
| *C07C 231/12* | (2006.01) | |
| *C07C 309/14* | (2006.01) | |
| *A61Q 5/12* | (2006.01) | |

(52) U.S. Cl.
CPC ............... *A61K 8/44* (2013.01); *A61K 8/042* (2013.01); *A61K 8/442* (2013.01); *A61Q 5/00* (2013.01); *A61Q 19/00* (2013.01); *A61Q 19/10* (2013.01); *C07C 231/12* (2013.01); *C07C 237/12* (2013.01); *C07C 309/14* (2013.01); *A61Q 5/12* (2013.01); *A61Q 17/04* (2013.01)

(58) Field of Classification Search
None
See application file for complete search history.

(56) References Cited

U.S. PATENT DOCUMENTS

2004/0248812 A1  12/2004  Hanabusa et al.

FOREIGN PATENT DOCUMENTS

| CN | 102126984 A | 7/2011 |
|---|---|---|
| JP | 2000-256303 A | 9/2000 |
| JP | 2002-249756 A | 9/2002 |
| JP | 2004-323503 A | 11/2004 |
| JP | 2004-323505 A | 11/2004 |
| JP | 2006-515006 A | 5/2006 |
| JP | 2006-516555 A | 7/2006 |
| WO | WO 00/53576 A1 | 9/2000 |
| WO | WO 2004/068997 A2 | 8/2004 |

OTHER PUBLICATIONS

Combined Chinese Office Action and Search Report issued Jul. 14, 2015 in Patent Application No. 201380008721.0 (with English translation of categories of cited documents).
U.S. Appl. No. 14/452,892, filed Aug. 6, 2014, Hanabusa, et al.
International Search Report issued Apr. 23, 2013, in PCT/JP2013/053147.
Masahiro Suzuki, et al., "Novel family of low molecular weight hydrogelators based on L-lysine derivatives", Chem. Comm., 8, 2002, pp. 884-885.
Masahiro Suzuki, et al., "A Family of Low-Molecular-Weight Hydrogelators Based on L-Lysine Derivatives with a Positively Charged Terminal Group", Chem. Eur. J., 9, No. 1, 2003, pp. 348-354.
Masahiro Suzuki, et al., "L-Lysine-based supramolecular hydrogels containing various inorganic ions", Org. Biomol. Chem., 3, 2005, pp. 3073-3078.
Japanese Office Action issued on Jan. 4, 2017 in Patent Application No. 2013-557612 (with English translation).

*Primary Examiner* — Mina Haghighatian
*Assistant Examiner* — Erin Hirt
(74) *Attorney, Agent, or Firm* — Oblon, McClelland, Maier & Neustadt, L.L.P.

(57) ABSTRACT

Provided is a compound capable of gelling various aqueous compositions containing salt, acid and the like.
An amphoteric ion-type basic amino acid derivative represented by the formula (1A):

(1A)

wherein each substituent is as defined in DESCRIPTION, or a salt thereof.

20 Claims, No Drawings

BASIC AMINO ACID DERIVATIVE THAT DEMONSTRATES A GELLING ABILITY IN A WATER SYSTEM

CROSS REFERENCES TO RELATED APPLICATIONS

This application is a continuation of International Patent Application No. PCT/JP2013/053147, filed on Feb. 8, 2013, and claims priority to Japanese Patent Application Nos. 2012-025683 filed on Feb. 9, 2012 and 2012-146669 filed on Jun. 29, 2012, both of which are incorporated herein by reference in their entireties.

BACKGROUND OF THE INVENTION

Field of the Invention

The present invention relates to an amphoteric ion-type basic amino acid derivative that demonstrates a gelling ability in a water system.

Discussion of the Background

A method of controlling fluidity of compositions that are liquid at ambient temperature such as cosmetic agents, pharmaceuticals, agricultural chemicals, feeds, fertilizers, paints and the like, and processing them into a form fitted for diversified use objects is an industrially very important technique. When the fluidity of an aqueous composition is controlled, water-soluble polymers such as carboxyvinyl polymer, xanthan gum and the like are generally used. These compounds are poor in salt tolerance and acid resistance, and often have difficulty in gelling an aqueous composition containing a salt or an acid. While a water-soluble polymer needs to be homogeneously dissolved or dispersed when gelling an aqueous composition, water-soluble polymers are not easily dispersed in an aqueous composition and precipitate is sometimes produced.

On the other hand, while patent document 1 discloses that sugar derivative gels water containing an oil solution and alcohol, it does not describe gelling of an aqueous composition containing a salt or an acid. Patent document 2 discloses a gelling agent of a basic amino acid derivative. While this gelling agent can gel various solvents including organic solvents, no description is provided as to aqueous solution containing an acid.

Moreover, non-patent documents 1 and 2 disclose gelling ability of amino acid derivatives having a pyridinium salt structure. While these compounds can gel even an aqueous solution containing an acid or a salt, since they are cationic molecules, they show poor compatibility with anionic water-soluble polymers such as xanthan gum, carboxyvinyl polymer and the like, and have stability problem since precipitation occurs and water is separated from the obtained gel composition.

DOCUMENT LIST

Patent Documents patent document 1: JP-A-2002-249756
patent document 2: JP-A-2004-323505

Non-Patent Documents non-patent document 1: Org. Biomol. Chem. 2005, 3, 3073
non-patent document 2: Chem. Eur. J. 2003, 9, 348

SUMMARY OF THE INVENTION

Problems to be Solved by the Invention

The problem of the present invention is to provide a compound having a superior gelling ability, which can gel various aqueous compositions containing a salt, an acid and the like. A further problem is to provide a gel composition which is free of syneresis and has superior stability.

Means of Solving the Problems

The present inventors have conducted intensive studies in an attempt to solve the aforementioned problem, and found that a particular amphoteric ion-type basic amino acid derivative and an amine derivative gel various aqueous compositions containing a salt, an acid and the like, which resulted in the completion of the present invention.

Accordingly, the present invention is as follows.

[1] An amphoteric ion-type basic amino acid derivative represented by the formula (1A):

$$\underset{O}{\overset{R^5}{\underset{R^1}{\bigwedge}}}\underset{N}{\overset{COOR^4}{\bigwedge}}\underset{(\phantom{i})_n}{\overset{O}{\bigwedge}}\underset{N}{\overset{R^2}{\underset{R^6}{\bigwedge}}}\underset{(\phantom{i})_m}{\overset{R^3}{\bigwedge}}Y-X \quad (1A)$$

wherein
an acyl group represented by $R^1$—CO— is an acyl group derived from an optionally substituted saturated or unsaturated fatty acid having 6-18 carbon atoms;
$R^2$ and $R^3$ are each independently an optionally substituted saturated or unsaturated straight chain or branched chain hydrocarbon group having 1-6 carbon atoms, or
$R^2$ and $R^3$ optionally form, together with the nitrogen atom bonded thereto, an optionally substituted heterocycle;
$R^4$, $R^5$ and $R^6$ are each independently a hydrogen atom or an optionally substituted saturated or unsaturated straight chain or branched chain hydrocarbon group having 1-6 carbon atoms;
m is an integer of 1-20;
n is an integer of 1-4;
X is a sulfonic acid group or a carboxylic acid group; and
Y is an optionally substituted saturated or unsaturated straight chain or branched chain divalent hydrocarbon group having 1-8 carbon atoms, or a salt thereof (hereinafter to be also referred to as the amphoteric ion-type basic amino acid derivative of the present invention).

[2] The amphoteric ion-type basic amino acid derivative of the above-mentioned [1], wherein the acyl group represented by $R^1$—CO— is an acyl group derived from a saturated or unsaturated fatty acid having 6-18 carbon atoms;
$R^2$ and $R^3$ are each independently a saturated or unsaturated straight chain or branched chain hydrocarbon group having 1-6 carbon atoms, or
$R^2$ and $R^3$ optionally form, together with the nitrogen atom bonded thereto, a heterocycle;
$R^4$, $R^5$ and $R^6$ are each independently a hydrogen atom or a saturated or unsaturated straight chain or branched chain hydrocarbon group having 1-6 carbon atoms; and
Y is a saturated or unsaturated straight chain or branched chain divalent hydrocarbon group having 1-8 carbon atoms, or a salt thereof.

[3] The amphoteric ion-type basic amino acid derivative of the above-mentioned [1], which is represented by the formula (1):

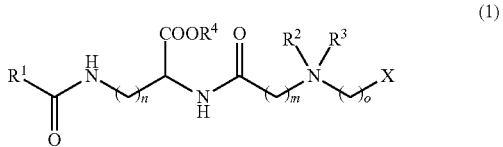

wherein
the acyl group represented by $R^1$—CO— is an acyl group derived from an optionally substituted saturated or unsaturated fatty acid having 6-18 carbon atoms;
$R^2$ and $R^3$ are each independently an optionally substituted saturated or unsaturated straight chain or branched chain hydrocarbon group having 1-6 carbon atoms, or
$R^2$ and $R^3$ optionally form, together with the nitrogen atom bonded thereto, an optionally substituted heterocycle;
$R^4$ is a hydrogen atom or an optionally substituted saturated or unsaturated straight chain or branched chain hydrocarbon group having 1-6 carbon atoms;
m is an integer of 1-20;
n is an integer of 1-4;
o is an integer of 1-8; and
X is a sulfonic acid group or a carboxylic acid group or a salt thereof.
[4] The amphoteric ion-type basic amino acid derivative of the above-mentioned [3], wherein the acyl group represented by $R^1$—CO— is an acyl group derived from a saturated or unsaturated fatty acid having 6-18 carbon atoms;
$R^2$ and $R^3$ are each independently a saturated or unsaturated straight chain or branched chain hydrocarbon group having 1-6 carbon atoms;
$R^4$ is a hydrogen atom or a saturated or unsaturated straight chain or branched chain hydrocarbon group having 1-6 carbon atoms;
m is an integer of 1-12; and
o is an integer of 1-6, or a salt thereof.
[5] The amphoteric ion-type basic amino acid derivative of any of the above-mentioned [1]-[4], wherein the acyl group represented by $R^1$—CO— is a lauroyl group and n is 4, or a salt thereof.
[6] The amphoteric ion-type basic amino acid derivative of any of the above-mentioned [1]-[5], wherein X is a sulfonic acid group, and $R^2$ and $R^3$ are methyl groups, or a salt thereof.
[7] The amphoteric ion-type basic amino acid derivative of the above-mentioned [1], which is selected from $N^\alpha$-(11-(N-(3-sulfopropyl)-N,N-dimethylamino)-undecanoyl)-$N^\epsilon$-lauroyl-L-lysine ethyl ester, $N^\alpha$-(11-(N-(3-sulfopropyl)-N,N-dimethylamino)-undecanoyl)-$N^\epsilon$-lauroyl-L-lysine methyl ester, $N^\alpha$-(11-(N-(4-sulfobutyl)-N,N-dimethylamino)-undecanoyl)-$N^\epsilon$-lauroyl-L-lysine methyl ester, $N^\alpha$-(11-(N-(4-sulfobutyl)-N,N-dimethylamino)-undecanoyl)-$N^\epsilon$-lauroyl-L-lysine ethyl ester, $N^\alpha$-(11-(N-carboxymethyl-N,N-dimethylamino)-undecanoyl)-$N^\epsilon$-lauroyl-L-lysine ethyl ester, $N^\alpha$-(11-(N-(2-carboxyethyl)-N,N-dimethylamino)-undecanoyl)-$N^\epsilon$-lauroyl-L-lysine ethyl ester, $N^\alpha$-(11-(N-(3-carboxypropyl)-N,N-dimethylamino)-undecanoyl)-$N^\epsilon$-lauroyl-L-lysine ethyl ester and $N^\alpha$-(11-(N-(4-carboxybutyl)-N,N-dimethylamino)-undecanoyl)-$N^\epsilon$-lauroyl-L-lysine ethyl ester, or a salt thereof.

[8] A gelling agent comprising at least one kind of the amphoteric ion-type basic amino acid derivatives of any of the above-mentioned [1]-[7] or a salt thereof.
[9] A gel composition comprising at least one kind of the amphoteric ion-type basic amino acid derivatives of any of the above-mentioned [1]-[7] or a salt thereof, and water.
[10] A cosmetic agent comprising the gel composition of the above-mentioned [9].
[11] A method of producing an amphoteric ion-type basic amino acid derivative represented by the formula (1A):

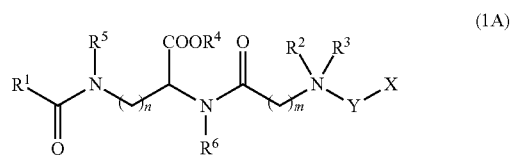

wherein
the acyl group represented by $R^1$—CO— is an acyl group derived from an optionally substituted saturated or unsaturated fatty acid having 6-18 carbon atoms;
$R^2$ and $R^3$ are each independently an optionally substituted saturated or unsaturated straight chain or branched chain hydrocarbon group having 1-6 carbon atoms, or
$R^2$ and $R^3$ optionally form, together with the nitrogen atom bonded thereto, an optionally substituted heterocycle;
$R^4$, $R^5$ and $R^6$ are each independently a hydrogen atom or an optionally substituted saturated or unsaturated straight chain or branched chain hydrocarbon group having 1-6 carbon atoms;
m is an integer of 1-20;
n is an integer of 1-4;
X is a sulfonic acid group or a carboxylic acid group; and
Y is an optionally substituted saturated or unsaturated straight chain or branched chain divalent hydrocarbon group having 1-8 carbon atoms, or a salt thereof, comprising using, as an intermediate, an amine derivative represented by the formula (2):

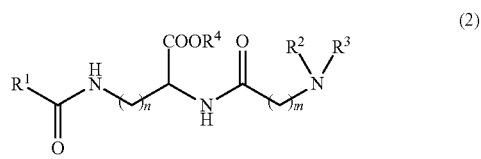

wherein
the acyl group represented by $R^1$—CO— is an acyl group derived from an optionally substituted saturated or unsaturated fatty acid having 6-18 carbon atoms;
$R^2$ and $R^3$ are each independently an optionally substituted saturated or unsaturated straight chain or branched chain hydrocarbon group having 1-6 carbon atoms, or
$R^2$ and $R^3$ optionally form, together with the nitrogen atom bonded thereto, an optionally substituted heterocycle;
$R^4$ is a hydrogen atom or an optionally substituted saturated or unsaturated straight chain or branched chain hydrocarbon group having 1-6 carbon atoms;
m is an integer of 1-20; and
n is an integer of 1-4,
or a salt thereof.

[12] An amine derivative represented by the formula (2):

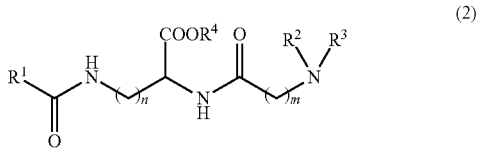

wherein
the acyl group represented by $R^1$—CO— is an acyl group derived from an optionally substituted saturated or unsaturated fatty acid having 6-18 carbon atoms;
$R^2$ and $R^3$ are each independently an optionally substituted saturated or unsaturated straight chain or branched chain hydrocarbon group having 1-6 carbon atoms, or
$R^2$ and $R^3$ optionally form, together with the nitrogen atom bonded thereto, an optionally substituted heterocycle;
$R^4$ is a hydrogen atom or an optionally substituted saturated or unsaturated straight chain or branched chain hydrocarbon group having 1-6 carbon atoms;
m is an integer of 1-20; and
n is an integer of 1-4, or a salt thereof (hereinafter to be also referred to as the amine derivative of the present invention).
[13] The amine derivative of the above-mentioned [12], wherein the acyl group represented by $R^1$—CO— is an acyl group derived from a saturated or unsaturated fatty acid having 6-18 carbon atoms;
$R^2$ and $R^3$ are each independently a saturated or unsaturated straight chain or branched chain hydrocarbon group having 1-6 carbon atoms,
$R^4$ is a hydrogen atom or a saturated or unsaturated straight chain or branched chain hydrocarbon group having 1-6 carbon atoms; and
m is an integer of 1-12, or a salt thereof.
[14] The amine derivative of the above-mentioned [12], which is selected from $N^\alpha$-(11-(N,N-dimethylamino)undecanoyl)-$N^\epsilon$-lauroyl-L-lysine ethyl ester and $N^\alpha$-(11-(N,N-dimethylamino)undecanoyl)-$N^\epsilon$-lauroyl-L-lysine methyl ester, or a salt thereof.
[15] A gelling agent comprising at least one kind of the amine derivatives of any of the above-mentioned [12]-[14] or a salt thereof.
[16] A gel composition comprising at least one kind of the amine derivatives of any of the above-mentioned [12]-[14] or a salt thereof, and water.
[17] A cosmetic agent comprising the gel composition of the above-mentioned [16].

Effect of the Invention

The amphoteric ion-type basic amino acid derivative and amine derivative of the present invention can gel various aqueous compositions containing a salt, an acid and the like. Furthermore, using the amphoteric ion-type basic amino acid derivative and amine derivative of the present invention, a gel composition which is free of syneresis and superior in stability can be provided. The gel composition controls fluidity of compositions that are liquid at ambient temperature such as cosmetic agents, pharmaceuticals, agricultural chemicals, feeds, fertilizers, paints and the like, and is useful for processing them into a form fitted for diversified use objects. Particularly, it is useful for cosmetic agents.

DETAILED DESCRIPTION OF THE PREFERRED EMBODIMENTS

In the present specification, the "demonstrates more superior gelling ability" refers to an ability to gel by the addition of a smaller amount thereof.
In the present specification, the "saturated or unsaturated fatty acid" means, unless otherwise specified, "saturated fatty acid" or "unsaturated fatty acid", and also encompasses "fatty acid derived from natural fats and oils".
In the present specification, examples of the saturated fatty acid contained in the "saturated or unsaturated fatty acid having 6-18 carbon atoms" include saturated straight chain fatty acids such as hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid and the like; saturated branched chain fatty acids such as isohexanoic acid, isoheptanoic acid, 2-ethylhexanoic acid, isononanoic acid, isodecanoic acid, dimethyloctanoic acid, isoundecanoic acid, isododecanoic acid, 2-butyloctanoic acid, isotridecanoic acid, isotetradecanoic acid, isopentadecanoic acid, isohexadecanoic acid, 2-hexyldecanoic acid, isoheptadecanoic acid, isostearic acid and the like; and cyclic fatty acids such as cyclohexanecarboxylic acid and the like.
In the present specification, examples of the unsaturated fatty acid contained in the "saturated or unsaturated fatty acid having 6-18 carbon atoms" include straight chain or branched chain unsaturated fatty acids such as undecenoic acid, myristoleic acid, palmitoleic acid, oleic acid, isooleic acid, linoleic acid, linolenic acid, elaidic acid and the like; and cyclic unsaturated fatty acids such as benzoic acid, nicotinic acid and the like.
In the present specification, examples of the natural fats and oils derived fatty acid contained in "saturated or unsaturated fatty acid having 6-18 carbon atoms" include coconut oil fatty acid, castor oil fatty acid, olive oil fatty acid and palm oil fatty acid and the like.
In the present specification, the "acyl group derived from fatty acid" means, unless otherwise specified, a substituent obtained by removing a hydroxyl group from a carboxy group of the above-mentioned "saturated fatty acid", "unsaturated fatty acid", "fatty acid derived from natural fats and oils" and the like.
In the present specification, examples of the "hydrocarbon group" include alkyl groups such as methyl group, ethyl group, propyl group, isopropyl group, butyl group, isobutyl group, sec-butyl group, tert-butyl group, pentyl group, isopentyl group, sec-pentyl group, tert-pentyl group, hexyl group, heptyl group, octyl group and the like, alkenyl groups such as vinyl group, 1-propen-1-yl group, 2-propen-1-yl group, isopropenyl group, 2-buten-1-yl group, 4-penten-1-yl group, 5-hexen-1-yl group and the like, and alkynyl groups such as ethynyl group, 1-propyn-1-yl group, 2-propyn-1-yl group, 4-pentyn-1-yl group, 5-hexyn-1-yl group and the like.
In the present specification, examples of the "divalent hydrocarbon group" include alkylene groups such as methylene group, ethylene group, 1-methylethylene group, trimethylene group, 2-methyltrimethylene group, tetramethylene group and the like, alkenylene groups such as vinylene group, 2-butene-1,4-diyl group, 1,2-dimethyl-1,2-ethenediyl group and the like, and alkynylene groups such as ethynylene group, 2-butyne-1,4-diyl group and the like.
In the present specification, the "heterocyclic group" shows, unless otherwise specified, a 5- to 14-membered monocyclic-tricyclic heterocyclic group containing, besides carbon atom, 1-4 hetero atoms selected from an oxygen atom, a sulfur atom and a nitrogen atom. Therein, any carbon atom as a ring atom may be substituted by an oxo group, and the sulfur atom or nitrogen atom may be oxidized to form an oxide. The hetero ring may be fused with a benzene ring, or crosslinked, or may form a Spiro ring.

In the present specification, examples of the "heterocycle" include rings corresponding to the above-mentioned "heterocyclic group".

In the present specification, examples of the "nitrogen-containing heterocycle" include, from the above-mentioned "heterocycle", a heterocycle having at least one nitrogen atom as a ring constituting atom can be mentioned.

In the present specification, examples of the "halogen atom" include a fluorine atom, a chlorine atom, a bromine atom, and an iodine atom.

In the present specification, examples of the substituent of the acyl group and hydrocarbon group include substituents selected from the following substituent group A. Examples of the substituent of the nitrogen-containing heterocycle include substituent selected from the following substituent group A and substituent group B. The number of the substituents is 1-substitutable maximum number, more preferably 1-3, further preferably 1.

In the present specification, substituent group A comprises
(a) a halogen atom;
(b) a hydroxy group;
(c) a nitro group;
(d) a cyano group;
(e) a $C_{3-7}$ cycloalkyl group;
(f) a $C_{6-14}$ aryl group;
(g) a $C_{7-16}$ aralkyl group;
(h) a heterocyclic group;
(i) a $C_{1-6}$ alkoxy group;
(j) a $C_{3-7}$ cycloalkyloxy group;
(k) a $C_{6-14}$ aryloxy group;
(l) a $C_{7-16}$ aralkyloxy group;
(m) a heterocyclyl-oxy group;
(n) an amino group optionally mono- or di-substituted by substituent(s) selected from the group consisting of a $C_{1-6}$ alkyl group, a $C_{2-6}$ alkenyl group, a $C_{6-14}$ aryl group, a $C_{7-16}$ aralkyl group, and a heterocyclic group;
(o) a $C_{1-6}$ alkyl-carbonyl group;
(p) a $C_{3-7}$ cycloalkyl-carbonyl group;
(q) a $C_{6-14}$ aryl-carbonyl group;
(r) a $C_{7-16}$ aralkyl-carbonyl group;
(s) a heterocyclyl-carbonyl group;
(t) a mono- or di-$C_{1-6}$ alkyl-carbamoyl group;
(u) a mono- or di-$C_{6-14}$ aryl-carbamoyl group; and
(v) a mono- or di-heterocyclyl-carbamoyl group.

In the present specification, substituent group B comprises
(a) a $C_{1-6}$ alkyl group;
(b) a $C_{2-6}$ alkenyl group; and
(c) a $C_{2-6}$ alkynyl group.

In the present specification, the substituent shown by

in each formula is also indicated as "$R^1$—CO-".

The amphoteric ion-type basic amino acid derivative of the present invention is a compound represented by the formula (1A) or a salt thereof.

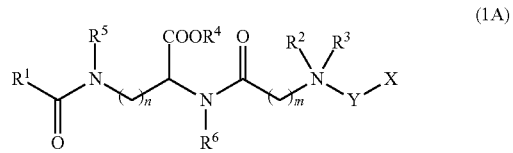

The amphoteric ion-type basic amino acid derivative of the present invention is preferably a compound of the formula (1) or a salt thereof.

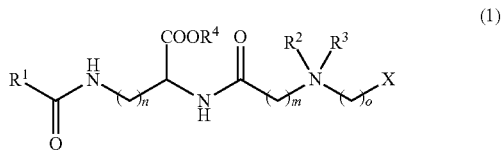

The definition of each symbol in the compounds represented by the formula (1A) and the formula (1) is explained in detail below.

The acyl group represented by $R^1$—CO— is an acyl group derived from an optionally substituted saturated or unsaturated fatty acid having 6-18 carbon atoms and, for example, hexanoyl group, heptanoyl group, octanoyl group, 2-ethylhexanoyl group, nonanoyl group, decanoyl group, lauroyl group, myristoyl group, palmitoyl group, stearoyl group, oleoyl group and linoleyl group can be mentioned, which are optionally substituted. The acyl group represented by $R^1$—CO— may be, besides an acyl group derived from fatty acid of a single composition, an acyl group derived from naturally-occurring mixed fatty acid or fatty acid obtained by synthesis (including branched fatty acid) such as coconut oil fatty acid, castor oil fatty acid, olive oil fatty acid, palm oil fatty acid and the like. One kind of these may be used, or two or more kinds selected from the above-mentioned groups may be used in a mixture. To demonstrate a more superior gelling ability, it is preferably an acyl group derived from saturated fatty acid having 6-18 carbon atoms, more preferably derived from straight chain or branched chain saturated fatty acid having 6-18 carbon atoms, further preferably a lauroyl group, a myristoyl group, a palmitoyl group or a stearoyl group, particularly preferably a lauroyl group.

$R^2$ and $R^3$ are each independently an optionally substituted saturated or unsaturated straight chain or branched chain hydrocarbon group having 1-6 carbon atoms, or $R^2$ and $R^3$ optionally form, together with the nitrogen atom bonded thereto, an optionally substituted nitrogen-containing heterocycle.

From the aspects of gelling ability and easiness of synthesis, $R^2$ and $R^3$ are preferably each independently a saturated or unsaturated straight chain or branched chain hydrocarbon group having 1-4 carbon atoms, more preferably a methyl group, an ethyl group or an isopropyl group, further preferably a methyl group.

In the formulas, $R^4$ is a hydrogen atom or an optionally substituted saturated or unsaturated straight chain or branched chain hydrocarbon group having 1-6 carbon atoms.

R[4] is preferably a hydrogen atom or a saturated or unsaturated straight chain or branched chain hydrocarbon group having 1-6 carbon atoms, more preferably a hydrogen atom or a saturated or unsaturated straight chain or branched chain hydrocarbon group having 1-4 carbon atoms, further preferably a hydrogen atom, methyl group, ethyl group or isopropyl group, particularly preferably a hydrogen atom, a methyl group or an ethyl group.

R[5] and R[6] are each independently a hydrogen atom or an optionally substituted saturated or unsaturated straight chain or branched chain hydrocarbon group having 1-6 carbon atoms.

R[5] and R[6] are each independently a hydrogen atom or a saturated or unsaturated straight chain or branched chain hydrocarbon group having 1-6 carbon atoms, and the both are more preferably hydrogen atoms.

Y is an optionally substituted saturated or unsaturated straight chain or branched chain divalent hydrocarbon group having 1-8 carbon atoms.

Y is preferably a saturated or unsaturated straight chain or branched chain divalent hydrocarbon group having 1-8 carbon atoms and, from the aspects of gelling ability and easiness of synthesis, it is more preferably a saturated or unsaturated straight chain or branched chain divalent hydrocarbon group having 1-6 carbon atoms, further preferably a saturated or unsaturated straight chain or branched chain divalent hydrocarbon group having 1-4 carbon atoms, particularly preferably a saturated or unsaturated straight chain or branched chain divalent hydrocarbon group having 3 or 4 carbon atoms (e.g., trimethylene, tetramethylene).

m is an integer of 1-20. From the aspect of gelling ability, m is preferably 1-12, more preferably 3-12, further preferably 7-12, particularly preferably 10.

n is an integer of 1-4. When n=3, it is an ornithine derivative and, when n=4, it is a lysine derivative. From the aspects of gelling ability and easiness of synthesis, n is preferably 3 or 4, particularly preferably 4 (lysine derivative).

o is an integer of 1-8. From the aspects of gelling ability and easiness of synthesis, o is preferably 1-6, more preferably 1-4, further preferably 3 or 4.

X is a sulfonic acid group or a carboxylic acid group. From the aspect of gelling ability, X is preferably a sulfonic acid group.

Preferable examples of the amphoteric ion-type basic amino acid derivative represented by the formula (1) include the following compounds.

(Compound-A)

A compound wherein an acyl group represented by R[1]—CO— is an acyl group derived from a straight chain or branched chain saturated fatty acid having 6-18 carbon atoms, R[2] and R[3] are each independently a saturated or unsaturated straight chain or branched chain hydrocarbon group carbon number 1-4, R[4] is a hydrogen atom or a saturated or unsaturated straight chain or branched chain hydrocarbon group having 1-4 carbon atoms, m is an integer of 3-12, n is an integer of 3 or 4, o is an integer of 1-6, and X is a sulfonic acid group or a carboxylic acid group.

(Compound-B)

A compound wherein an acyl group represented by R[1]—CO— is a lauroyl group, a myristoyl group, a palmitoyl group or a stearoyl group, R[2] and R[3] are each independently a methyl group, an ethyl group or an isopropyl group, R[4] is a hydrogen atom, a methyl group, an ethyl group or an isopropyl group, m is an integer of 7-12, n is an integer of 4, o is an integer of 1-4, and X is a sulfonic acid group or a carboxylic acid group.

(Compound-C)

A compound wherein an acyl group represented by R[1]—CO— is a lauroyl group,

R[2] and R[3] are methyl groups,

R[4] is a hydrogen atom, a methyl group or an ethyl group, m is an integer of 10, n is an integer of 4, o is an integer of 3 or 4, and X is a sulfonic acid group or a carboxylic acid group.

Examples of the salt of the amphoteric ion-type basic amino acid derivative of the present invention include a salt with cation and a salt with anion depending on the pH and the like. Examples of the salt with cation include alkali metal salts such as lithium salt, sodium salt, potassium salt and the like; alkaline earth metal salts such as calcium salt, magnesium salt and the like; ammonium salts such as alkanolamine salt and the like; basic organic salt and the like. Of these, sodium salt, potassium salt or ammonium salt is preferable, sodium salt or potassium salt is more preferable, and sodium salt is further preferable, from the aspect of solubility. Examples of the salt with anion include inorganic ion salts such as hydrochloride, sulfate, phosphate, hydrobromide and the like; and organic compound salts such as acetate, maleate, fumarate, succinate, methanesulfonate, p-toluenesulfonate, citrate, tartrate and the like. Of these, hydrochloride, sulfate, phosphate, acetate or citrate is desirable, hydrochloride, sulfate or citrate is more desirable, and hydrochloride is further desirable.

Since the amphoteric ion-type basic amino acid derivative of the present invention is an amphoteric ion-type compound, even when the above-mentioned cation or anion is absent depending on the pH, a salt is considered to be formable intramolecularly or intermolecularly.

Examples of the amphoteric ion-type basic amino acid derivative of the present invention include the following.

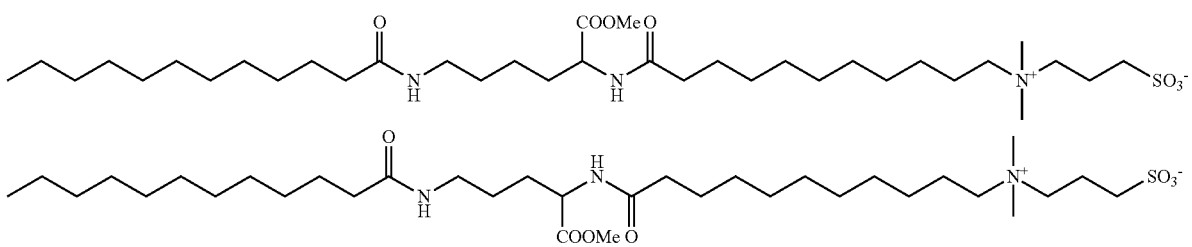

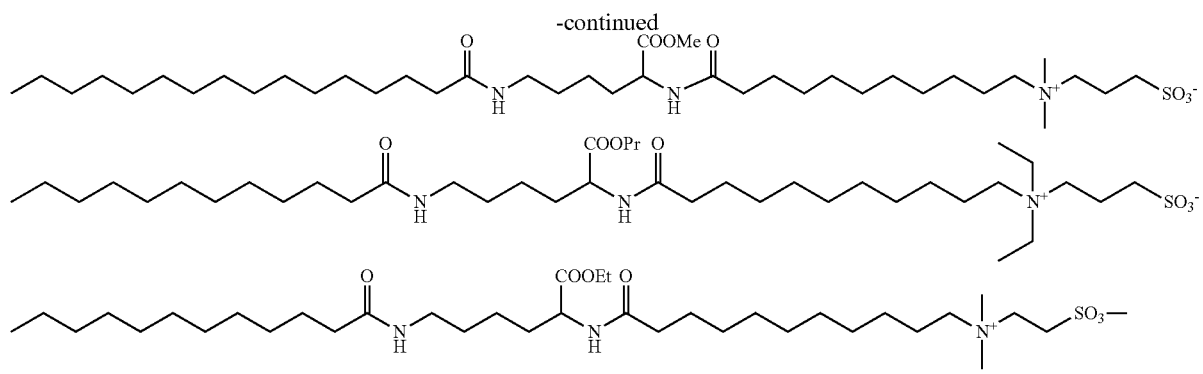

The amphoteric ion-type basic amino acid derivative of the present invention is preferably one or more kinds selected from $N^\alpha$-(11-(N-(3-sulfopropyl)-N,N-dimethylamino)-undecanoyl)-$N^\epsilon$-lauroyl-L-lysine ethyl ester, $N^\alpha$-(11-(N-(3-sulfopropyl)-N,N-dimethylamino)-undecanoyl)-$N^\epsilon$-lauroyl-L-lysine methyl ester, $N^\alpha$-(11-(N-(4-sulfobutyl)-N,N-dimethylamino)-undecanoyl)-$N^\epsilon$-lauroyl-L-lysine methyl ester, $N^\alpha$-(11-(N-(4-sulfobutyl)-N,N-dimethylamino)-undecanoyl)-$N^\epsilon$-lauroyl-L-lysine ethyl ester, $N^\alpha$-(11-(N-carboxymethyl-N,N-dimethylamino)-undecanoyl)-$N^\epsilon$-lauroyl-L-lysine ethyl ester, $N^\alpha$-(11-(N-(2-carboxyethyl)-N,N-dimethylamino)-undecanoyl)-$N^\epsilon$-lauroyl-L-lysine ethyl ester, $N^\alpha$-(11-(N-(3-carboxypropyl)-N,N-dimethylamino)-undecanoyl)-$N^\epsilon$-lauroyl-L-lysine ethyl ester and $N^\alpha$-(11-(N-(4-carboxybutyl)-N,N-dimethylamino)-undecanoyl)-$N^\epsilon$-lauroyl-L-lysine ethyl ester and salts thereof, more preferably one or more kinds of selected from $N^\alpha$-(11-(N-(3-sulfopropyl)-N,N-dimethylamino)-undecanoyl)-$N^\epsilon$-lauroyl-L-lysine ethyl ester, $N^\alpha$-(11-(N-(3-sulfopropyl)-N,N-dimethylamino)-undecanoyl)-$N^\epsilon$-lauroyl-L-lysine methyl ester, $N^\alpha$-(11-(N-(4-sulfobutyl)-N,N-dimethylamino)-undecanoyl)-$N^\epsilon$-lauroyl-L-lysine methyl ester, $N^\alpha$-(11-(N-(4-sulfobutyl)-N,N-dimethylamino)-undecanoyl)-$N^\epsilon$-lauroyl-L-lysine ethyl ester and salts thereof.

The amphoteric ion-type basic amino acid derivative of the present invention can be synthesized by a conventional method. For example, acyl amino acid such as $N^\epsilon$-lauroyl lysine and the like is used as a starting material, which is esterified and reacted with acid chloride wherein the terminal is halogenated, and then reacted with secondary amine, and with sultone or lactone, whereby the derivative is prepared. In addition, it can also be prepared by reacting the material with secondary amine to give the compound of the formula (2), and reacting same with the corresponding sulfonic acid or carboxylic acid.

As the sultone and lactone, a commercially available product can be directly used, or one produced according to a method known per se, or a method analogous thereto, can also be used. Sultone and lactone optionally have 1-5 substituents selected from the above-mentioned substituent group A and the above-mentioned substituent group B.

Particularly, sultone is preferably used and, for example, 1,1-methanesultone, 1,2-ethanesultone, 1,3-propanesultone, prop-1-ene-1,3-sultone, 1,4-butanesultone, 2,4-butanesultone, 1,5-pentanesultone or 1,6-hexanesultone can be used. It is preferably one or more kinds selected from 1,1-methanesultone, 1,2-ethanesultone, 1,3-propanesultone and 1,4-butanesultone, more preferably 1,3-propanesultone or 1,4-butanesultone.

One synthetic example of amphoteric ion-type basic amino acid derivative wherein X is a sulfonic acid group of the present invention is shown below.

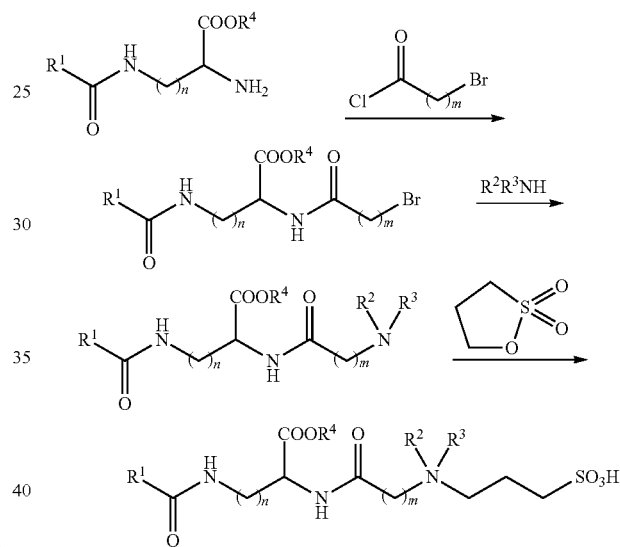

wherein $R^1$, $R^2$, $R^3$, $R^9$, m and n are as defined for the formula (1).

As another embodiment, one embodiment of the synthetic example of the amphoteric ion-type basic amino acid derivative of the present invention is shown below.

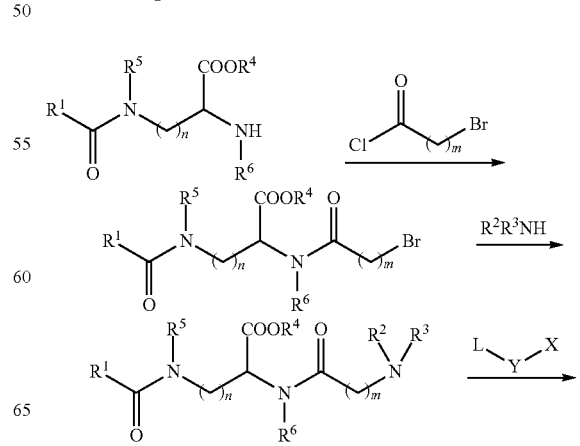

-continued

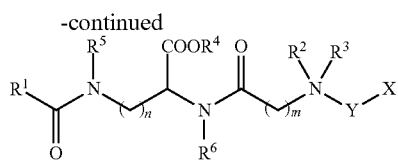

wherein $R^1$-$R^6$, X, Y, m and n are as defined for the formula (1A) and the formula (1), and L is a leaving group (e.g., chlorine atom, bromine atom).

The amine derivative represented by the following formula (2) is useful as an intermediate for the amphoteric ion-type basic amino acid derivative of the present invention. In addition, the amine derivative itself represented by the formula (2) also has a gelling ability, and can be used as a gelling agent. Moreover, it can be used by mixing with a compound of the formula (1).

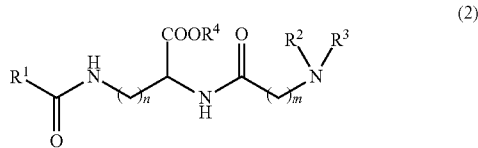

(2)

wherein $R^1$, $R^2$, $R^3$, $R^4$, m and n are as defined for the formula (1A) and the formula (1).

As the salt of the amine derivative of the present invention, salts similar to the salts of the above-mentioned amphoteric ion-type basic amino acid derivative of the present invention can be mentioned.

The present invention also relates to a gelling agent containing the above-mentioned amphoteric ion-type basic amino acid derivative. In the present specification, the gelling agent refers to a substance that thickens a liquid and changes into a jelly or solid form. In the present invention, it is particularly useful as a gelling agent for an aqueous composition. The "aqueous composition" in the present invention means a composition containing water.

Examples of the form of the gelling agent include solid, particle, solution and paste. Excipients and solvents can be used as appropriate. When a solution form is desired, acids such as hydrochloric acid, citric acid, phosphoric acid and the like and bases such as sodium hydroxide and the like can be used to adjust the pH as appropriate. The pH of the gelling agent is preferably 1-14, the upper limit is preferably 13, more preferably 12, and the lower limit is preferably 2, more preferably 3, from the aspect of solubility.

The gelling agent of the present invention is added to an aqueous composition, the mixture is heated to 40-100° C. as necessary, homogeneously stirred, and left standing at room temperature to allow the aqueous composition to be gelled or thickened. The gel hardness or viscosity can be freely adjusted by controlling the amount of the gelling agent of the present invention to be added.

While the amount of the gelling agent to be added to an aqueous composition varies depending on the constitution of the aqueous composition, it is added to 0.0001 wt %-20 wt %, in the weight concentration of the amphoteric ion-type basic amino acid derivative.

The lower limit is more preferably 0.001 wt %, further preferably 0.01 wt %, further more preferably 0.1 wt %, especially preferably 1 wt %. The upper limit is more preferably 15 wt %, further preferably 10 wt %, further more preferably 7 wt %, especially preferably 5 wt %.

The pH for preparation of the gel is preferably 1-14. From the aspect of solubility, the upper limit is preferably 13, more preferably 12, and the lower limit is preferably 2, more preferably 3.

The present invention also relates to a gel composition comprising at least one kind of the above-mentioned amphoteric ion-type basic amino acid derivatives and salts thereof, and water. The gel composition of the present invention is superior in stability. In the present specification, "superior in stability" means that precipitate is not found in the gel preparation step and after preparation, and syneresis does not occur with the progress of time.

The gel composition of the present invention can contain other gelling agents or solidifying agents as long as the effect of the present invention is not impaired. Examples of other gelling agents or solidifying agents include natural polymers such as alginic acid, carageenan, agar, guar gum, curdlan, xanthan gum, pullulan, gellan gum, gelatin, casein, albumin, collagen and the like, semisynthetic polymers such as methylcellulose, ethylcellulose, hydroxyethylcellulose, hydroxypropylcellulose, carboxymethylcellulose, methylhydroxypropylcellulose, soluble starch, carboxymethylstarch, methylstarch, alginic acid propyleneglycol ester and the like, synthetic polymers such as polyvinyl alcohol, polyacrylic acid salt, polyvinylpyrrolidone, polyvinyl methylether, carboxyvinylpolymer, sodium polyacrylate, polyethylene oxide, ethyleneoxide•propyleneoxide block copolymer and the like, inorganic substances such as bentonite, laponite, finely divided powder silicon dioxide, colloidal alumina and the like, and the like.

The present invention further relates to a cosmetic agent containing the above-mentioned gel composition. Specific examples of the cosmetic agent of the present invention include adiaphoretic, facial cleanser, cleansing gel, milky lotion, massage cream, cold cream, moisture gel, facial mask, after shaving gel, foundation, chapstick, lipstick, cheek, mascara, shampoo, rinse, hair tonic, treatment, conditioner, tic, set lotion, hair cream, hair wax, hair mousse, perm solution, hair dye, hair coloring, hair manicure, sunscreen oil, hand soap, aromatic and the like.

The cosmetic agent of the present invention can contain various components usable for general cosmetic agent, skin external preparation or quasi-drug as long as the effect of the present invention is not inhibited. Examples thereof include oily component, chelating agent, surfactant, powder, amino acid, amino acid derivative, polyamino acid, lower alcohol, higher alcohol, polyvalent alcohol, sugar alcohol and alkyleneoxide adduct thereof, water-soluble polymer, plant extract, nucleic acid, vitamin, enzyme, gelling agent, humectant, disinfectant and antimicrobial agent, anti-inflammatory agent, analgesic, antifungal agent, stratum corneum softening release agent, skin colorant, hormone agent, ultraviolet ray absorbent, hair tonic, antiperspirant and astringent active ingredient, perspiration deodorant, vitamin, vasodilator, crude drug, pH adjuster, sequestrant, viscosity modifier, pearl ingredient, natural perfume, synthetic perfume, dye, pigment, antioxidant, preservative, emulsifier, fat, wax, silicone compound, balm and the like.

EXAMPLES

The present invention is explained in more detail in the following by referring to Examples, which are not to be construed as limitative.

The instruments used for the measurement of the compound are as described below. IR measuring apparatus: JASCO FS-420 spectrometer, 1H-NMR: Bruker AVANCE400 spectrometer, elemental analysis apparatus: Perkin-Elmer series II CHNS/O analyzer 2400.

Production Example 1

Step 1; Synthesis of $N^\alpha$-(11-(N,N-dimethylamino)undecanoyl)-$N^\epsilon$-lauroyl-L-lysine ethyl ester ($C_2AmiC_{11}NMe_2$)

$N^\alpha$-(11-bromoundecanoyl)-$N^\epsilon$-lauroyl-L-lysine ethyl ester (10 g) described in non-patent document 2 (Chem. Eur. J. 2003, 9, 348-354) was dissolved in about 11 wt % dimethylamine ethanol solution (200 mL), and the mixture was stirred under a nitrogen atmosphere in an ice bath for 1 hr, at room temperature for 1 hr, at 35° C. for 1 day, and at 45° C. for 2 days. The reaction m solution was dried under reduced pressure, and the obtained solid was dissolved in chloroform. The mixture was partitioned 3 times with saturated aqueous sodium hydrogen carbonate solution, and the chloroform layer was dried over magnesium sulfate, and the solution was evaporated to dryness. The crude product was recrystallized from ethanol-ether to give the title compound (yield (7.5 g, 80%)).

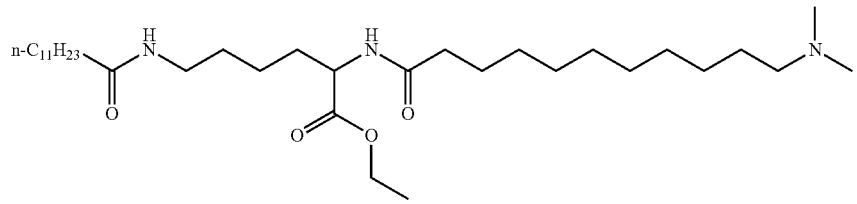

FT-IR(KBr): ν=3308, 1742, 1640, 1546, 1524 cm$^{-1}$. $^1$H-NMR (400 MHz, CDCl$_3$, TMS, 25° C.): δ=0.88 (t, J=6.7 Hz, 3H), 1.26-1.34 (m, 31H), 1.44-1.49 (m, 2H), 1.51-1.56 (m, 2H), 1.51-1.62 (m, 6H), 1.65-1.88 (m, 2H), 2.15 (t, J=7.3 Hz, 2H), 2.27-2.28 (m, 10H), 3.21-3.26 (m, 2H), 4.19 (q, J=7.1 Hz, 2H), 4.53-4.59 (m, $^1$H), 5.64 (br, 1H), 6.11 (d, J=7.8 Hz, 1H). Elemental Analysis calcd (%) for C$_{33}$H$_{65}$N$_3$O$_4$ (567.89): C, 69.79; H, 11.54; N, 7.40. Found: C, 69.81; H, 11.67; N, 7.51.

Step 2; Synthesis of $N^\alpha$-(11-(N-(3-sulfopropyl)-N,N-dimethylamino)-undecanoyl)-$N^\epsilon$-lauroyl-L-lysine ethyl ester ($C_2AmiC_{11}NMe_2C_3SO_3$)

$C_2AmiC_{11}NMe_2$ (3.25 g) obtained above was dissolved in dehydrated acetonitrile (100 mL), 0.7 g of 1,3-propanesultone was slowly added with stirring. This was stirred under a nitrogen atmosphere at 50° C. for 12 hr. The mixture was stood at room temperature and the precipitated crystals were collected by filtration. The crude product was recrystallized from ethanol-ether. yield (3.6 g, 92%).

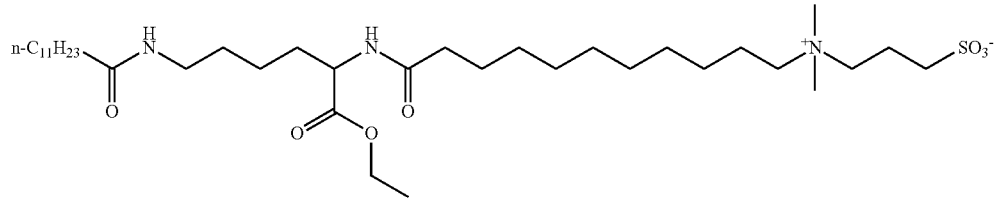

FT-IR(KBr): ν=3450, 3312, 1730, 1642, 1543 cm$^{-1}$. $^1$H-NMR (400 MHz, CDCl$_3$, TMS, 25° C.): δ=0.88 (t, J=6.6 Hz, 3H), 1.27-1.48 (m, 35H), 1.51-1.61 (m, 4H), 1.72-1.86 (m, 6H), 2.16 (t, J=7.0 Hz, 2H), 2.25 (t, J=7.4 Hz, 4H), 2.92 (t, J=6.6 Hz, 2H), 3.18 (s, 6H), 3.12-3.24 (m, 2H), 3.27-3.36 (m, 2H), 4.17 (q, J=7.1 Hz, 2H), 4.47-4.52 (m, 1H), 6.07 (t, J=5.6 Hz, 1H), 6.58 (d, J=7.6 Hz, 1H). Elemental Analysis calcd (%) for C$_{36}$H$_{71}$N$_3$O$_7$S (690.03): C, 62.66; H, 10.37; N, 6.09. Found: C, 63.12; H, 10.54; N, 6.17.

Production Example 2

Step 1; Synthesis of $N^\alpha$-(11-(N,N-dimethylamino)undecanoyl)-$N^\epsilon$-lauroyl-L-lysine methyl ester ($C_1AmiC_{11}NMe_2$)

Synthesized using $N^\alpha$-(11-bromoundecanoyl)-$N^\epsilon$-lauroyl-L-lysine methyl ester (10 g) described in non-patent document 2 (Chem. Eur. J. 2003, 9, 348-354) and by a method similar to Production Example 1. yield (7.5 g, 80%).

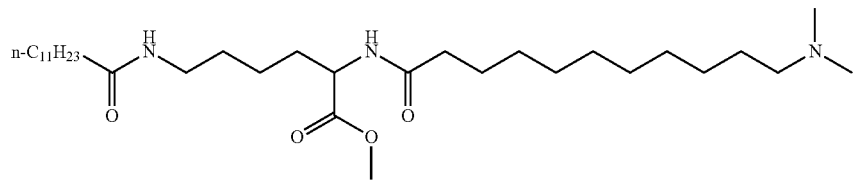

FT-IR(KBr): $\nu$=3308, 1741, 1640, 1546 cm$^{-1}$. $^1$H-NMR (400 MHz, CDCl$_3$, TMS, 25° C.): $\delta$=0.88 (t, J=6.6 Hz, 3H), 1.25-1.27 (m, 32H), 1.49-1.86 (m, 8H), 2.16 (t, J=8.2, 2H), 2.21-2.26 (m, 2H), 2.76 (s, 6H), 2.93-2.98 (m, 2H), 3.23 (q, J=6.0 Hz, 2H), 3.65 (s, 3H), 4.52-4.22 (m, 1H), 5.71 (t, J=5.6 Hz, 1H), 6.20 (d, J=7.8 Hz, 1H). Elemental Analysis calcd (%) for $C_{32}H_{63}N_3O_4$ (553.86): C, 69.39; H, 11.47; N, 7.59. Found: C, 70.01; H, 11.66; N, 7.69.

Step 2; Synthesis of $N^\alpha$-(11-(N-(3-sulfopropyl)-N,N-dimethylamino)-undecanoyl)-$N^\epsilon$-lauroyl-L-lysine methyl ester ($C_1AmiC_{11}NMe_2C_3SO_3$)

Synthesized using $C_1AmiC_{11}NMe_2$ (3.25 g) obtained above and by a method similar to Production Example 1. yield (3.5 g, 90%).

FT-IR(KBr): $\nu$=3308, 1741, 1640, 1546 cm-$^1$. $^1$H-NMR (400 MHz, CDCl$_3$, TMS, 25° C.): $\delta$=0.88 (t, J=7.0 Hz, 3H), 1.25-1.38 (m, 30H), 1.48-1.59 (m, 6H), 1.68-1.84 (m, 4H), 2.14-2.18 (m, 2H), 2.25 (t, J=7.4 Hz, 4H), 2.92 (t, J=6.6 Hz, 2H), 3.17 (s, 6H), 3.20-3.24 (m, 2H), 3.27-3.31 (m, 2H), 3.45 (s, 3H), 3.78-3.82 (m, 2H), 4.47-4.53 (m, 1H), 6.04 (t, J=5.6 Hz, 1H), 6.55 (d, J=7.6 Hz, 1H). Elemental Analysis calcd (%) for $C_{35}H_{69}N_3O_7S$ (676.00): C, 62.19; H, 10.29; N, 6.22. Found: C, 62.12; H, 10.54; N, 6.25.

Production Example 3

Synthesis of $N^\alpha$-(11-(N-(4-sulfobutyl)-N,N-dimethylamino)-undecanoyl)-$N^\epsilon$-lauroyl-L-lysine methyl ester ($C_1AmiC_{11}NMe_2C_4SO_3$)

$C_1AmiC_{11}NMe_2$ (2.47 g, 4.45 mmol) prepared in Production Example 2, Step 1, was dissolved in dehydrated acetonitrile (100 mL), and 1,4-butanesultone (0.61 g, 4.45 mmol) was slowly added with stirring. This was stirred under a nitrogen atmosphere at 50° C. for 48 hr. The mixture was stood at room temperature and the precipitated crystals were collected by filtration. The crude product was recrystallized from ethanol-ether. yield (2.50 g, 80%).

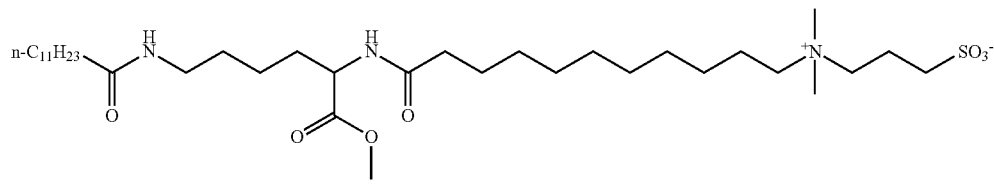

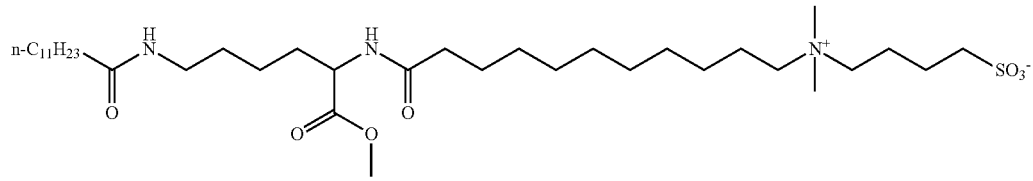

FT-IR(KBr): ν=3308, 1740, 1640, 1547, 1188 cm$^{-1}$.
$^1$H-NMR (400 MHz, CDCl$_3$, TMS, 25° C.): δ=0.86 (t, J=6.8 Hz, 3H), 1.25-1.30 (m, 26H), 1.34-1.38 (m, 6H), 1.49-1.55 (m, 2H), 1.59-1.63 (m, 4H), 1.72-1.83 (m, 4H), 2.16 (t, J=7.0 Hz, 4H), 2.25 (t, J=7.3 Hz, 4H), 2.90 (t, J=6.6 Hz, 2H), 3.19 (s, 6H), 3.28-3.33 (m, 2H), 3.71 (s, 3H), 3.72-3.77 (m, 2H), 4.47-4.52 (m, 1H), 6.16 (t, J=5.6 Hz, 1H), 6.73 (d, J=7.6 Hz, 1H). Elemental Analysis calcd (%) for C$_{36}$H$_{71}$N$_3$O$_7$S (690.03): C, 62.66; H, 10.37; N, 6.09. Found: C, 62.88; H, 10.64; N, 6.10.

Production Example 4

Synthesis of N$^α$-(11-(N-(4-sulfobutyl)-N,N-dimethylamino)-undecanoyl)-N$^ε$-lauroyl-L-lysine ethyl ester (C$_2$AmiC$_{11}$NMe$_2$C$_4$SO$_3$)

C$_2$AmiC$_{11}$NMe$_2$ (2.53 g, 4.45 mmol) synthesized in Production Example 1, Step 1, was dissolved in dehydrated acetonitrile (100 mL), and 1,4-butanesultone (0.61 g, 4.45 mmol) was slowly added with stirring. This was stirred under a nitrogen atmosphere at 50° C. for 48 hr. The mixture was stood at room temperature and the precipitated crystals were collected by filtration. The crude product was recrystallized from ethanol-ether. yield (2.71 g, 86%).

C$_{37}$H$_{73}$N$_3$O$_7$S (704.06): C, 63.12; H, 10.45; N, 5.97. Found: C, 63.29; H, 10.66; N, 6.05.

Production Example 5

Synthesis of N$^α$-(11-(N-carboxymethyl-N,N-dimethylamino)-undecanoyl)-N$^ε$-lauroyl-L-lysine ethyl ester (C$_2$AmiC$_{11}$NMe$_2$CO$_2$)

C$_2$AmiC$_{11}$NMe$_2$ (1.4 g) synthesized in Production Example 1, Step 1, was dissolved in distilled ethanol (70 mL), and sodium chloroacetate (0.3 g) dissolved in 10 mL of pure water was added with stirring. This was stirred under a nitrogen atmosphere at 70° C. overnight. This was concentrated under reduced pressure, and hot filtered several times with ethanol. This was recrystallized from ethanol-ether. yield (1.19 g, 77%).

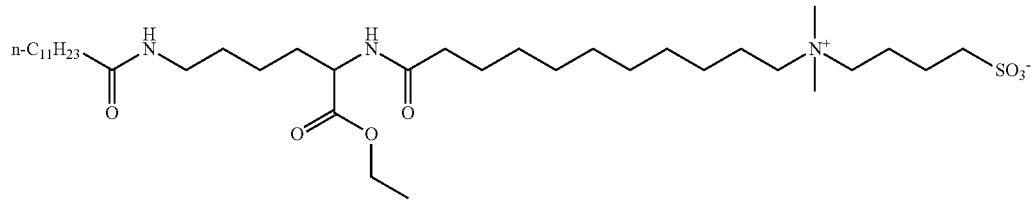

FT-IR(KBr): ν=3308, 1740, 1640, 1546, 1186 cm$^{-1}$.
$^1$H-NMR (400 MHz, CDCl$_3$, TMS, 25° C.): δ=0.86 (t, J=6.9 Hz, 3H), 1.25-1.27 (m, 25H), 1.34-1.39 (m, 6H), 1.48-1.55 (m, 4H), 1.56-1.67 (m, 6H), 1.72-1.83 (m, 4H), 2.14-2.18 (m, 2H), 2.25 (t, J=7.4 Hz, 4H), 2.91-2.94 (m, 2H), 3.17 (s, 6H), 3.27-3.32 (m, 4H), 3.77-3.82 (m, 2H), 4.17 (q, J=7.1 Hz, 2H), 4.47-4.53 (m, 1H), 6.04 (t, J=5.7 Hz, 1H), 6.55 (d, J=7.6 Hz, 1H). Elemental Analysis calcd (%) for

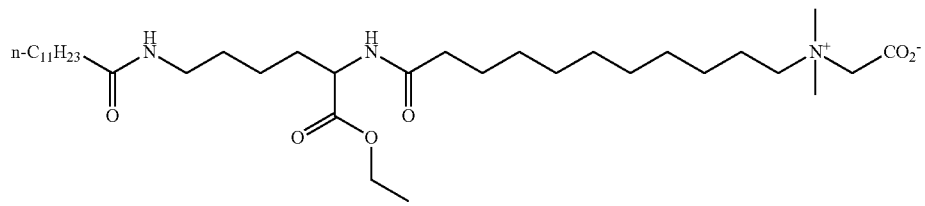

FT-IR(KBr): ν=3308, 1741, 1641, 1547 cm$^{-1}$. $^1$H-NMR (400 MHz, DMSO, TMS): δ=0.84 (t, 3H, J=6.7 Hz), 1.23-1.36 (m, 35H), 1.46-1.52 (m, 4H), 1.45-1.51 (m, 4H), 1.56-1.62 (m, 2H), 1.99-2.03 (m, 2H), 2.10 (s, 6H), 2.11-2.16 (m, 4H), 2.96 (t, 2H, J=6.4 Hz), 4.05-4.08 (m, 2H), 4.13-4.17 (m, 1H), 7.71 (t, 1H, J=5.6 Hz), 8.07 (d, 1H, J=7.6 Hz). Elemental Analysis calcd (%) for $C_{35}H_{67}N_3O_6$ (625.92); C, 67.16; H, 10.79; N, 6.71. found, C, 68.87; H, 10.93; N, 6.77.

Production Example 6

Synthesis of N$^α$-(11-(N-(2-carboxyethyl)-N,N-dimethylamino)-undecanoyl)-N$^ε$-lauroyl-L-lysine ethyl ester ($C_2AmiC_{11}NMe_2C_2O_2$)

Synthesized using $C_2AmiC_{11}NMe_2$ synthesized in Production Example 1, Step 1, and sodium 3-chloropropionate, and by a method similar to $C_2AmiC_{11}NMe_2CO_2$. yield (0.60 g, 71%).

FT-IR(KBr): ν=3307, 1740, 1640, 1547 cm$^{-1}$. $^1$H-NMR (400 MHz, DMSO, TMS): δ=0.84 (t, 3H, J=6.8 Hz), 1.23-1.31 (m, 35H), 1.34-1.40 (m, 4H), 1.46-1.50 (m, 4H), 1.59-1.66 (m, 2H), 2.00-2.04 (m, 2H), 2.12 (s, 6H), 2.17-2.21 (m, 4H), 2.99 (t, 2H, J=6.6 Hz), 3.17-3.23 (m, 4H), 4.04-4.08 (m, 2H), 4.11-4.17 (m, 1H), 7.71 (t, 1H, J=5.5 Hz), 8.08 (d, 1H, J=7.5 Hz). Elemental Analysis calcd (%) for $C_{37}H_{71}N_3O_6$ (653.98); C, 67.95; H, 10.94; N, 6.43. found, C, 67.22; H, 10.87; N, 6.32.

Production Example 8

Synthesis of N$^α$-(11-(N-(4-carboxybutyl)-N,N-dimethylamino)-undecanoyl)-N$^ε$-lauroyl-L-lysine ethyl ester ($C_2AmiC_{11}NMe_2C_4O_2$)

Synthesized using $C_2AmiC_{11}NMe_2$ synthesized in Production Example 1, Step 1, and sodium 5-chloropentanoate, and by a method similar to $C_2AmiC_{11}NMe_2CO_2$. yield (0.75 g, 75%).

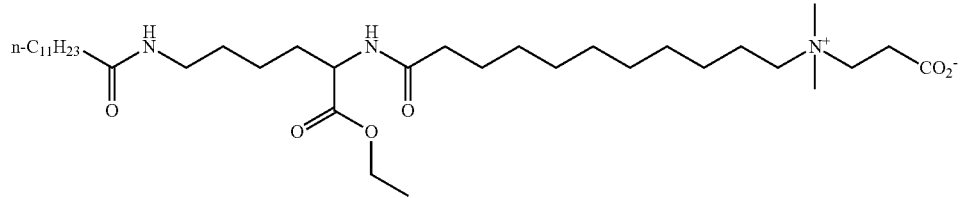

FT-IR(KBr): ν=3305, 1740, 1640, 1547 cm$^{-1}$. $^1$H-NMR (400 MHz, DMSO, TMS): b=0.84 (t, 3H, J=6.8 Hz), 1.23-1.31 (m, 35H), 1.35-1.50 (m, 4H), 1.57-1.64 (m, 2H), 1.99-2.03 (m, 2H), 2.08 (s, 6H), 2.11-2.17 (m, 4H), 2.97 (t, 2H, J=6.2 Hz), 3.21-3.31 (m, 4H), 3.60 (s, 2H), 4.04-4.06 (m, 2H), 4.13-4.17 (m, 1H), 7.70 (t, 1H, J=5.5 Hz), 8.06 (d, 1H, J=7.4 Hz). Elemental Analysis calcd (%) for $C_{36}H_{69}N_3O_6$ (625.92); C, 67.57; H, 10.87; N, 6.57. found, C, 67.11; H, 10.65; N, 6.43.

Production Example 7

Synthesis of N$^α$-(11-(N-(3-carboxypropyl)-N,N-dimethylamino)-undecanoyl)-N$^ε$-lauroyl-L-lysine ethyl ester ($C_2AmiC_{11}NMe_2C_3O_2$)

Synthesized using $C_2AmiC_{11}NMe_2$ synthesized in Production Example 1, Step 1, and sodium 4-chlorobutyrate, and by a method similar to $C_2AmiC_{11}NMe_2CO_2$. yield (0.68 g, 68%).

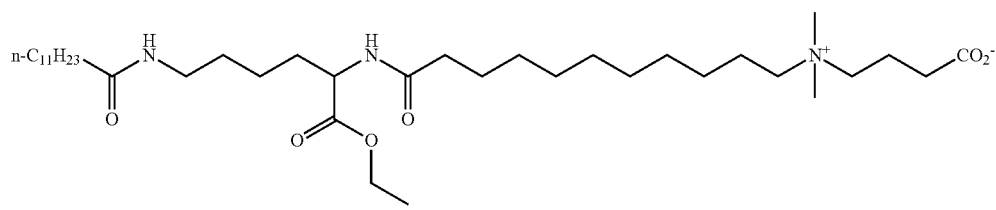

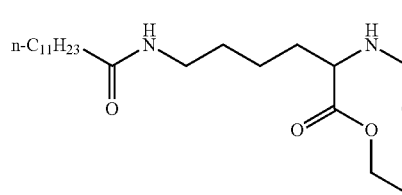

FT-IR(KBr): ν=3313, 1744, 1640, 1552 cm$^{-1}$. $^1$H-NMR (400 MHz, DMSO, TMS): δ=0.84 (t, 3H, J=6.8 Hz), 1.23-1.31 (m, 37H), 1.34-1.42 (m, 4H), 1.43-1.49 (m, 4H), 1.55-1.66 (m, 2H), 2.00-2.03 (m, 2H), 2.08 (s, 6H), 2.10-2.17 (m, 4H), 2.97 (t, 2H, J=6.6 Hz), 3.17-3.23 (m, 4H), 4.04-4.08 (m, 2H), 4.13-4.17 (m, 1H), 7.71 (t, 1H, J=5.7 Hz), 8.07 (d, 1H, J=7.5 Hz). Elemental Analysis calcd (%) for $C_{38}H_{73}N_3O_6$ (668.00); C, 68.32; H, 11.01; N, 6.29. found, C, 68.00; H, 10.90; N, 6.27.

<Gelling Ability of Various Derivatives>

The gelling ability of the amphoteric ion-type basic amino acid derivatives prepared in Production Examples 1-8 was confirmed. Test tube equipped with a cover was filled with water, saline, phosphate buffered saline (hereinafter indicated as PBS), and aqueous NaCl solution or aqueous KCl solution, and an amphoteric ion-type basic amino acid derivative was added at various concentrations. The mixture was heated to 100° C. to achieve homogeneous dissolution, and stood at 25° C. for 2 hr. After allowing to cool, the vial was tilted, and the absence of fluidity was judged as gellation, and the appearance was visually observed.

The results are shown below.

Abbreviations mean the following.

GT: transparent gel
GTL: translucent gel
GO: opaque gel

The number in the parenthesis shows minimum gelling concentration (g/L).

Gelling Ability of Amphoteric Ion-Type Basic Amino Acid Derivative of Production Example 1
water: GTL(2), saline: GTL(4), PBS: GTL(2), 0.1M hydrochloric acid: GTL(4), 1.0M hydrochloric acid: GT(4), 0.1M phosphoric acid: GTL(2), 1.0M phosphoric acid: GT(4), 0.1M acetic acid: GTL(2), 1.0M acetic acid: GO(4), 0.1M aqueous NaCl solution: GTL(8), 1.0M aqueous NaCl solution: GT(2), 0.1M aqueous KCl solution: GTL(8), 1.0M aqueous KCl solution: GT(2), 0.1M aqueous MgCl$_2$ solution: GTL(8), 1.0M aqueous MgCl$_2$ solution: GT(2), 0.1M aqueous CaCl$_2$ solution: GTL(4), 1.0M aqueous CaCl$_2$ solution: GT(4)

Gelling Ability of Amphoteric Ion-Type Basic Amino Acid Derivative of Production Example 2
water: GT(2), saline: GTL(2), PBS: GTL(4), 0.1M hydrochloric acid: GTL(2), 1.0M hydrochloric acid: GTL(2), 0.1M phosphoric acid: GTL(2), 1.0M phosphoric acid: GO(4), 0.1M acetic acid: GT(2), 1.0M acetic acid: GTL(4), 0.1M aqueous NaCl solution: GTL(2), 1.0M aqueous NaCl solution: GT(2), 0.1M aqueous KCl solution: GTL(10), 1.0M aqueous KCl solution: GT(2), 0.1M aqueous MgCl$_2$ solution: GTL(4), 1.0M aqueous MgCl$_2$ solution: GT(2), 0.1M aqueous CaCl$_2$ solution: GTL(4), 1.0M aqueous CaCl$_2$ solution: GT(2)

Gelling Ability of Amphoteric Ion-Type Basic Amino Acid Derivative of Production Example 3
water: GT(2), saline: GTL(8), PBS: GO(4), 0.1M hydrochloric acid: GT(2), 1.0M hydrochloric acid: GTL(2), 0.1M phosphoric acid: GT(4), 1.0M phosphoric acid: GO(4), 0.1M acetic acid: GT(4), 1.0M acetic acid: GT(4), 0.1M aqueous NaCl solution: GO(40), 1.0M aqueous NaCl solution: GTL(20), 0.1M aqueous KCl solution: GO(40), 1.0M aqueous KCl solution: GTL(40), 0.1M aqueous MgCl$_2$ solution: GTL(8), 1.0M aqueous MgCl$_2$ solution: GTL(8), 0.1M aqueous CaCl$_2$ solution: GTL(20), 1.0M aqueous CaCl$_2$ solution: GTL(8)

Gelling Ability of Amphoteric Ion-Type Basic Amino Acid Derivative of Production Example 4
water: GT(2), saline: GO(40), PBS: GTL(8), 0.1M hydrochloric acid: GT(2), 1.0M hydrochloric acid: GTL(4), 0.1M phosphoric acid: GT(2), 1.0M phosphoric acid: GTL(2), 0.1M acetic acid: GO(8), 1.0M acetic acid: GO(8), 0.1M aqueous NaCl solution: GO(40), 1.0M aqueous NaCl solution: GTL(20), 0.1M aqueous KCl solution: GTL(40), 1.0M aqueous KCl solution: GTL(40), 0.1M aqueous MgCl$_2$ solution: GTL(8), 1.0M aqueous MgCl$_2$ solution: GTL(8), 0.1M aqueous CaCl$_2$ solution: GTL(20), 1.0M aqueous CaCl$_2$ solution: GTL(8)

Gelling Ability of Amphoteric Ion-Type Basic Amino Acid Derivative of Production Example 5
water: GTL(2), 0.1M hydrochloric acid: GTL(8), 1.0M hydrochloric acid: GTL(2), 0.1M sulfuric acid: GO(10), 1.0M sulfuric acid: GTL(8), 0.1M phosphoric acid: GT(2), 1.0M phosphoric acid: GT(2), 0.1M acetic acid: GTL(8), 1.0M acetic acid: GT(8)

Gelling Ability of Amphoteric Ion-Type Basic Amino Acid Derivative of Production Example 6
water: GT(2), saline: GO(10), PBS: GO(20), 0.1M hydrochloric acid: GTL(8), 1.0M hydrochloric acid: GTL(2), 0.1M sulfuric acid: GTL(4), 1.0M sulfuric acid: GTL(2), 0.1M phosphoric acid: GTL(10), 1.0M phosphoric acid: GT(2), 0.1M acetic acid: GT(2), 1.0M acetic acid: GT(2), 0.1M aqueous NaCl solution: GO(10), 0.1M aqueous KCl solution: GTL(4), 0.1M aqueous MgCl$_2$ solution: GTL(4), 0.1M aqueous CaCl$_2$ solution: GTL(10)

Gelling Ability of Amphoteric Ion-Type Basic Amino Acid Derivative of Production Example 7
water: GT(1), saline: GTL(10), PBS: GO(40), 0.1M hydrochloric acid: GT(1), 1.0M hydrochloric acid: GTL(2), 0.1M sulfuric acid: GTL(8), 1.0M sulfuric acid: GTL(2), 0.1M phosphoric acid: GT(2), 1.0M phosphoric acid: GT(2), 0.1M acetic acid: GT(2), 1.0M acetic acid: GT(4), 0.1M aqueous NaCl solution: GTL(2), 0.1M aqueous KCl solution: GTL(2), 0.1M aqueous MgCl$_2$ solution: GTL(10), 0.1M aqueous CaCl$_2$ solution: GTL(10)

Gelling Ability of Amphoteric Ion-Type Basic Amino Acid Derivative of Production Example 8
water: GT(1), saline: GTL(4), PBS: GO(40), 0.1M hydrochloric acid: GT(1), 1.0M hydrochloric acid: GTL(40), 0.1M sulfuric acid: GTL(8), 1.0M sulfuric acid: GTL(2), 0.1M phosphoric acid: GT(2), 1.0M phosphoric acid: GT(2), 0.1M acetic acid: GT(2), 1.0M acetic acid: GT(4), 0.1M aqueous NaCl solution: GTL(1), 0.1M aqueous KCl solution: GTL(1), 0.1M aqueous MgCl$_2$ solution: GTL(2), 0.1M aqueous CaCl$_2$ solution: GTL(2)

It was clarified that the amphoteric ion-type basic amino acid derivative of the present invention can gel various aqueous compositions by the addition of a small amount thereof.

Also, C$_2$AmiC$_{11}$NMe$_2$, which is the intermediate for the amphoteric ion-type basic amino acid derivative of Production Example 1, was confirmed to have the following gelling ability. water: GO(20), saline: GTL(10), PBS: GTL(10), 0.1M hydrochloric acid: GTL(10), 1.0M hydrochloric acid: GTL(10), 0.1M phosphoric acid: GO(10), 1.0M phosphoric acid: GTL(8), 0.1M acetic acid: GO(10), 1.0M acetic acid: GTL(10), 0.1M aqueous NaCl solution: GTL(10), 0.1M aqueous KCl solution: GTL(10), 0.1M aqueous MgCl$_2$ solution: GTL(10), 0.1M aqueous CaCl$_2$ solution: GTL(8)

Formulation Example 1

Preparation of Skin Lotion Gel

Components A shown below were dissolved by mixing at 70° C., and component B was gradually added at 70° C. Components C mixed by heating to 70° C. were further added, and the mixture was cooled to give a gelled skin lotion. The prepared skin lotion showed no syneresis even after 1 week of storage at room temperature and was stable.

TABLE 1

|   |   | (mass %) |
|---|---|---|
| A | di(phytosteryl/octyldodecyl)lauroylglutamate *1 | 0.35 |
|   | cetyl octanoate | 0.15 |
|   | PPG-8-ceteth-20 *2 | 0.50 |
|   | PPG-6-decyltetradeceth-30 *3 | 0.50 |
|   | glycerol | 1.25 |
| B | water | 5.00 |
| C | DPG | 2.00 |
|   | BG | 3.00 |
|   | Compound of Production Example 2 | 0.20 |
|   | citric acid | q.s. |
|   | water | balance |
|   |   | 100.00 |

*1 "Eldew PS-203" (manufactured by Ajinomoto Co., Inc.)
*2 "Nikkol PBC-44" (manufactured by Nikko Chemicals)
*3 "Nikkol PEN-4630" (manufactured by Nikko Chemicals)

Formulation Example 2

Preparation of Cream

Components A, components B and components C shown below were each dissolved at 85° C., and components A were added to components B with stirring at 85° C. Components C were further added, and the mixture was cooled to give a cream.

TABLE 2

| A | polyglyceryl-10 myristate *1 | 2.20 |
|---|---|---|
|   | polyglyceryl-6 stearate *2 | 1.10 |
|   | preservative | as required |
|   | squalane | 6.00 |
|   | shea butter | 2.00 |
|   | macadamia nut oil | 4.00 |
|   | di(phytosteryl/octyldodecyl)lauroylglutamate *3 | 0.50 |

TABLE 2-continued

| B | stearic acid | 4.00 |
|---|---|---|
|   | cetanol | 3.50 |
|   | octyldodecanol | 3.20 |
|   | BG | 5.00 |
|   | dibutyllauroyl glutamide *4 | 0.48 |
|   | dibutylethylhexanoyl glutamide *5 | 0.32 |
| C | arginine | 0.05 |
|   | compound of Production Example 1 | 0.30 |
|   | preservative | as required |
|   | water | balance |
|   |   | 100.00 |

*1 "Nikkol Decaglyn 1-M" (manufactured by Nikko Chemicals)
*2 "Nikkol Hexaglyn 1-S" (manufactured by Nikko Chemicals)
*3 "Eldew PS-203" (manufactured by Ajinomoto Co., Inc.)
*4 "GP-1" (manufactured by Ajinomoto Co., Inc.)
*5 "EB-21" (manufactured by Ajinomoto Co., Inc.)

Formulation Example 3

Preparation of Milky Lotion

Components C shown below were dispersed, and added to components B to give an aqueous phase. The aqueous phase was heated to 80° C., components A heated in the same manner were added, and the mixture was emulsified. Components D were further added, and the mixture was emulsified and cooled with stirring to room temperature to give a milky lotion.

TABLE 3

| A | triethylhexanoin | 3.00 |
|---|---|---|
|   | dimethicone | 1.50 |
|   | glyceryl stearate | 0.50 |
|   | polyglyceryl distearate *1 | 1.50 |
|   | myristoylmethyl-β-alanine(phytosteryl/decyltetradecyl) *2 | 3.00 |
| B | glycerol | 20.00 |
|   | BG | 10.00 |
|   | hydrogenated lecithin | 0.50 |
|   | preservative | q.s. |
|   | water | balance |
| C | (acrylic acid/alkyl acrylate (C10-30)) copolymer *3 | 0.10 |
|   | water | 9.90 |
| D | arginine | 0.10 |
|   | compound of Production Example 3 | 0.20 |
|   | water | 5.00 |
|   |   | 100.00 |

*1 "Emalex OTG" (manufactured by Nihon Emulsion Co., Ltd.)
*2 "Eldew APS-307" (manufactured by (Ajinomoto Co., Inc.)
*3 "Carbopol ETD-2020" (manufactured by Lubrizol)

Formulation Example 4

Preparation of Hair Treatment

Component B shown below was sufficiently dispersed in component A, components C were added to component A, and the mixture was dissolved by stirring with heating. Separately-heated components D were gradually added to emulsify the mixture. After cooling, components E were added to prepare a hair treatment.

TABLE 4

| A | purified water | balance |
|---|---|---|
| B | hydroxyethylcellulose | 0.02 |

TABLE 4-continued

| | | |
|---|---|---|
| C | lactic acid | 0.01 |
| | methylparaben | 0.2 |
| | EDTA-2Na | 0.05 |
| D | steartrimonium chloride | 2.00 |
| | cetanol | 4.00 |
| | hexyldecyl isostearate | 2.00 |
| E | PCA-Na *1 | 4.00 |
| | water | 10.00 |
| | compound of Production Example 2 | 0.20 |
| | dimethicone | 2.00 |
| | flavor | q.s. |
| | | 100.00 |

*1 "AJIDEW NL-50" (manufactured by Ajinomoto Co., Inc.)

Formulation Example 5

Preparation of Sunscreen

Components A shown below were dissolved by heating, and components C were added. Components B were further added, and the mixture was sufficiently dispersed to give an oil phase. Components D were separately dissolved by heating. After cooling, the mixture was added to the oil phase at room temperature to emulsify the mixture, whereby a sunscreen was prepared.

TABLE 5

| | | |
|---|---|---|
| A | isopropyl lauroylsarcosinate *1 | 5.80 |
| | glyceryl tri(capryl/capric acid) | 15.00 |
| | dimethicone *2 | 2.00 |
| | isononyl isononanoate | 2.00 |
| | triisostearic acid PEG-10 hydrogenated castor oil *3 | 3.00 |
| | PEG-11 methyletherdimethicone *4 | 1.50 |
| | triisostearic acid PEG-20 hydrogenated castor oil *5 | 0.50 |
| | oxybenzone-3 *6 | 5.00 |
| B | zinc oxide *7 | 5.00 |
| | titanium oxide *8 | 5.00 |
| | lauroyllysine*9 | 1.00 |
| C | quarternium-18 bentonite *10 | 1.00 |
| | glyceryl tri(capryl/capric acid) | 9.00 |
| | isopropyl lauroylsarcosinate | 0.20 |
| D | NaCl | 0.50 |
| | phenoxyethanol | 0.30 |
| | compound of Production Example 3 | 0.05 |
| | water | balance |
| | | 100.00 |

*1 "Eldew SL-205" (manufactured by Ajinomoto Co., Inc.)
*2 "TSF451-5A" (manufactured by Momentive Performance Materials Inc.)
*3 "Emalex RWIS-310" (manufactured by Nihon Emulsion Co., Ltd.)
*4 "KF-351A" (manufactured by Shin-Etsu silicone)
*5 "Emalex RWIS-320" (manufactured by Nihon Emulsion Co., Ltd.)
*6 "Escalol 567" (manufactured by ISP)
*7 "MZ-303S" (manufactured by Tayca)
*8 "MT-100Z" (manufactured by Tayca)
*9 "Amihope LL" (manufactured by Ajinomoto Co., Inc.)
*10 "S-BEN(W)" (manufactured by HOJUN Co., Ltd.)

Formulation Example 6

Preparation of Facial Cleanser

Components A shown below were dissolved by heating, components B, C and D were added in this order, and the mixture was cooled. Component E was further added to prepare a facial cleanser.

TABLE 6

| | | |
|---|---|---|
| A | cocoylglutamic acid K (30%) *1 | 15.0 |
| | cocoylalanine Na (30%) *2 | 25.0 |
| | lauroylmethylalanine Na (30%) *3 | 10.0 |
| | myristic acid K | 1.0 |
| | lauryl glycol hydroxypropylether *4 | 2.0 |
| | BG | 3.0 |
| | glycerol | 2.0 |
| | glyceryl laurate | 2.0 |
| | water | balance |
| | compound of Production Example 1 | 0.5 |
| | glycol distearate *5 | 1.0 |
| | preservative | q.s. |
| B | hydroxypropylmethylcellulose *6 | 1.0 |
| C | magnesium chloride | 0.5 |
| D | citric acid (20% aqueous solution) | 5.6 |
| E | flavor | q.s. |
| | | 100.00 |

*1 "Amisoft CK-22" (manufactured by Ajinomoto Co., Inc.)
*2 "Amilite ACS-12" (manufactured by Ajinomoto Co., Inc.)
*3 "Alanone ALE" (manufactured by Kawaken Fine Chemicals)
*4 "Viscosafe LPE" (manufactured by Kawaken Fine Chemicals)
*5 "Emalex EG-di-SE" (manufactured by Nihon Emulsion Co., Ltd.)
*6 "Metolose 60SH-4000" (Shin-Etsu Chemical Co., Ltd.)

INDUSTRIAL APPLICABILITY

Using the compound of the present invention, various aqueous compositions containing salt, acid and the like can be gelled, and a stable gel composition can be provided. The gel composition can be used as a cosmetic agent.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (1 A):

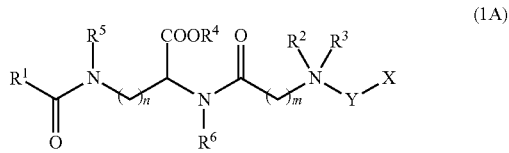

wherein
R$^1$—CO— is an acyl group derived from an optionally substituted saturated or unsaturated fatty acid having 6 to 18 carbon atoms;
R$^2$ and R$^3$ are each independently an optionally substituted saturated or unsaturated, straight chain or branched chain hydrocarbon group having 1 to 6 carbon atoms, or
R$^2$ and R$^3$ form, together with the nitrogen atom to which they are bonded, an optionally substituted heterocycle;
R$^4$, R$^5$, and R$^6$ are each independently a hydrogen atom or an optionally substituted saturated or unsaturated, straight chain or branched chain hydrocarbon group having 1 to 6 carbon atoms;

m is an integer of 1 to 20;

n is an integer of 1 to 4;

X is a sulfonic acid group or a carboxylic acid group; and

Y is an optionally substituted saturated or unsaturated, straight chain or branched chain divalent hydrocarbon group having 1 to 8 carbon atoms, or a salt thereof.

2. The compound according to claim 1, wherein $R^1$—CO— is an acyl group derived from a saturated or unsaturated fatty acid having 6 to 18 carbon atoms;

$R^2$ and $R^3$ are each independently a saturated or unsaturated, straight chain or branched chain hydrocarbon group having 1 to 6 carbon atoms, or $R^2$ and $R^3$ form, together with the nitrogen atom to which they are bonded, a heterocycle;

$R^4$, $R^5$, and $R^6$ are each independently a hydrogen atom or a saturated or unsaturated, straight chain or branched chain hydrocarbon group having 1 to 6 carbon atoms; and Y is a saturated or unsaturated, straight chain or branched chain divalent hydrocarbon group having 1 to 8 carbon atoms, or a salt thereof.

3. The compound according to claim 1, which is represented by formula (1):

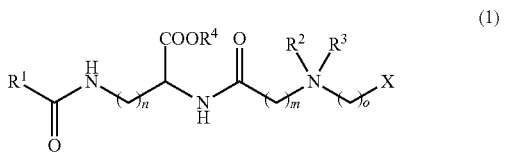

(1)

wherein $R^1$—CO— is an acyl group derived from an optionally substituted saturated or unsaturated fatty acid having 6 to 18 carbon atoms;

$R^2$ and $R^3$ are each independently an optionally substituted saturated or unsaturated, straight chain or branched chain hydrocarbon group having 1 to 6 carbon atoms, or $R^2$ and $R^3$ form, together with the nitrogen atom to which they are bonded, an optionally substituted heterocycle;

$R^4$ is a hydrogen atom or an optionally substituted saturated or unsaturated, straight chain or branched chain hydrocarbon group having 1 to 6 carbon atoms;

m is an integer of 1 to 20;

n is an integer of 1 to 4;

o is an integer of 1 to 8; and

X is a sulfonic acid group or a carboxylic acid group, or a salt thereof.

4. The compound according to claim 3, wherein $R^1$—CO— is an acyl group derived from a saturated or unsaturated fatty acid having 6 to 18 carbon atoms;

$R^2$ and $R^3$ are each independently a saturated or unsaturated, straight chain or branched chain hydrocarbon group having 1 to 6 carbon atoms;

$R^4$ is a hydrogen atom or a saturated or unsaturated, straight chain or branched chain hydrocarbon group having 1 to 6 carbon atoms;

m is an integer of 1 to 12; and o is an integer of 1 to 6, or a salt thereof.

5. The compound according to claim 1, wherein $R^1$—CO— is a lauroyl group and n is 4, or a salt thereof.

6. The compound according to claim 2, wherein $R^1$—CO— is a lauroyl group and n is 4, or a salt thereof.

7. The compound according to claim 3, wherein $R^1$—CO— is a lauroyl group and n is 4, or a salt thereof.

8. The compound according to claim 4, wherein $R^1$—CO— is a lauroyl group and n is 4, or a salt thereof.

9. The compound according to claim 1, wherein X is a sulfonic acid group, and $R^2$ and $R^3$ are methyl groups, or a salt thereof.

10. The compound according to claim 2, wherein X is a sulfonic acid group, and $R^2$ and $R^3$ are methyl groups, or a salt thereof.

11. The compound according to claim 3, wherein X is a sulfonic acid group, and $R^2$ and $R^3$ are methyl groups, or a salt thereof.

12. The compound according to claim 4, wherein X is a sulfonic acid group, and $R^2$ and $R^3$ are methyl groups, or a salt thereof.

13. The compound according to claim 5, wherein X is a sulfonic acid group, and $R^2$ and $R^3$ are methyl groups, or a salt thereof.

14. A gelling agent, comprising at least one compound according to claim 1 or a salt thereof.

15. A gel composition, comprising at least one compound according to claim 1 or a salt thereof, and water.

16. A cosmetic agent, comprising a gel composition according to claim 15.

17. A method of producing a compound represented by formula (1A):

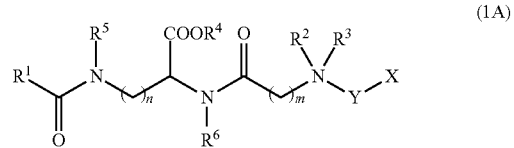

(1A)

wherein $R^1$—CO— is an acyl group derived from an optionally substituted saturated or unsaturated fatty acid having 6 to 18 carbon atoms;

$R^2$ and $R^3$ are each independently an optionally substituted saturated or unsaturated, straight chain or branched chain hydrocarbon group having 1 to 6 carbon atoms, or $R^2$ and $R^3$ form, together with the nitrogen atom to which they are bonded, an optionally substituted heterocycle;

$R^4$, $R^5$, and $R^6$ are each independently a hydrogen atom or an optionally substituted saturated or unsaturated, straight chain or branched chain hydrocarbon group having 1 to 6 carbon atoms;

m is an integer of 1 to 20;

n is an integer of 1 to 4;

X is a sulfonic acid group or a carboxylic acid group; and

Y is an optionally substituted saturated or unsaturated, straight chain or branched chain divalent hydrocarbon group having 1 to 8 carbon atoms, or a salt thereof, said method comprising converting a compound represented by formula (2):

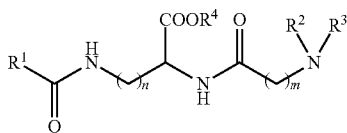

(2)

wherein

R¹—CO— is an acyl group derived from an optionally substituted saturated or unsaturated fatty acid having 6 to 18 carbon atoms;

R² and R³ are each independently an optionally substituted saturated or unsaturated, straight chain or branched chain hydrocarbon group having 1 to 6 carbon atoms, or R² and R³ form, together with the nitrogen atom to which they are bonded thereto, an optionally substituted heterocycle;

R⁴ is a hydrogen atom or an optionally substituted saturated or unsaturated, straight chain or branched chain hydrocarbon group having 1 to 6 carbon atoms;

m is an integer of 1 to 20; and n is an integer of 1 to 4, or a salt thereof, into said compound represented by formula (1A).

18. The compound according to claim 1, wherein
R¹—CO— is an acyl group derived from an unsubstituted, saturated or unsaturated fatty acid having 6 to 18 carbon atoms,
or a salt thereof.

19. The compound according to claim 1, wherein
R¹—CO— is an acyl group selected from the group consisting of a lauroyl group, a myristoyl group, a palmitoyl group, and a stearoyl group,
or a salt thereof.

20. A compound, which is selected from the group consisting of:
$N^\alpha$-(11-(N-(3-sulfopropyl)-N,N-dimethylamino)-undecanoyl)-$N^\epsilon$-lauroyl-L-lysine ethyl ester,
$N^\alpha$-(11-(N-(3-sulfopropyl)-N,N-dimethylamino)-undecanoyl)-$N^\epsilon$-lauroyl-L-lysine methyl ester,
$N^\alpha$-(11-(N-(4-sulfopropyl)-N,N-dimethylamino)-undecanoyl)-$N^\epsilon$-lauroyl-L-lysine methyl ester,
$N^\alpha$-(11-(N-(4-sulfobutyl)-N,N-dimethylamino)-undecanoyl)-$N^\epsilon$-lauroyl-L-lysine ethyl ester,
$N^\alpha$-(11-(N-(carboxymethyl-N,N-dimethylamino)-undecanoyl)-$N^\epsilon$-lauroyl-L-lysine ethyl ester,
$N^\alpha$-(11-(N-(2-carboxyethyl)-N,N-dimethylamino)-undecanoyl)-$N^\epsilon$-lauroyl-L-lysine ethyl ester,
$N^\alpha$-(11-(N-(3-carboxypropyl)-N,N-dimethylamino)-undecanoyl)-$N^\epsilon$-lauroyl-L-lysine ethyl ester, and
$N^\alpha$-(11-(N-(4-carboxybutyl)-N,N-dimethylamino)-undecanoyl)-$N^\epsilon$lauroyl-L-lysine ethyl ester,
or a salt thereof.

* * * * *

UNITED STATES PATENT AND TRADEMARK OFFICE
CERTIFICATE OF CORRECTION

PATENT NO. : 9,750,676 B2
APPLICATION NO. : 14/453036
DATED : September 5, 2017
INVENTOR(S) : Kenji Hanabusa et al.

Page 1 of 1

It is certified that error appears in the above-identified patent and that said Letters Patent is hereby corrected as shown below:

In the Claims

In Claim 20:
Column 32, Line 17 "4-sulfopropyl" should read --4-sulfobutyl--
Column 32, Line 23 "N ,N -dimethylamino" should read --N,N-dimethylamino--
Column 32, Line 24 "N $^\varepsilon$-lauroyl-L" should read --N$^\varepsilon$-lauroyl-L"--

Signed and Sealed this
Eleventh Day of June, 2019

Andrei Iancu
*Director of the United States Patent and Trademark Office*